(12) United States Patent
Ren et al.

(10) Patent No.: US 10,180,424 B2
(45) Date of Patent: Jan. 15, 2019

(54) ENHANCEMENT SOLUTION FOR ENHANCING CHEMILUMINESCENCE AND METHOD FOR PREPARING CHEMILUMINESCENT SOLUTION

(71) Applicant: Shenzhen Maxchemtech Co., Ltd., Shenzhen, Guangdong (CN)

(72) Inventors: Qi Ren, Guangdong (CN); Jian Li, Guangdong (CN)

(73) Assignee: SHENZHEN MAXCHEMTECH CO., LTD., Shenzhen, Guangdong (CN)

( * ) Notice: Subject to any disclaimer, the term of this patent is extended or adjusted under 35 U.S.C. 154(b) by 205 days.

(21) Appl. No.: 15/246,771

(22) Filed: Aug. 25, 2016

(65) Prior Publication Data
US 2017/0016887 A1    Jan. 19, 2017

Related U.S. Application Data

(63) Continuation of application No. PCT/CN2015/096022, filed on Nov. 30, 2015.

(30) Foreign Application Priority Data

Nov. 5, 2014  (CN) .......................... 2014 1 0617881

(51) Int. Cl.
  C09K 11/07   (2006.01)
  G01N 33/532  (2006.01)
  C09K 9/02    (2006.01)

(52) U.S. Cl.
  CPC .............. G01N 33/532 (2013.01); C09K 9/02 (2013.01); C09K 11/07 (2013.01); C09K 2211/1007 (2013.01); C09K 2211/1022 (2013.01); C09K 2211/1029 (2013.01); C09K 2211/1033 (2013.01)

(58) Field of Classification Search
  CPC ........ G01N 33/532; C09K 11/07; C09K 9/02; C09K 2211/1022; C09K 2211/1029; C09K 2211/1007; C09K 2211/1033
  See application file for complete search history.

(56) References Cited

U.S. PATENT DOCUMENTS

| 5,145,772 | A | 9/1992 | Voyta et al. |
| 5,474,725 | A | 12/1995 | Akhavan-Tafti |
| 5,547,836 | A | 8/1996 | Bronstein et al. |
| 6,767,716 | B2 | 7/2004 | Giri |
| 8,557,147 | B2 * | 10/2013 | Qian ...................... C09K 11/06 252/700 |
| 2001/0005584 | A1 | 6/2001 | Matsuno et al. |
| 2002/0013250 | A1 | 1/2002 | Giri |
| 2004/0259182 | A1 | 12/2004 | Edwards et al. |
| 2017/0016887 | A1 * | 1/2017 | Ren ...................... G01N 33/532 |

FOREIGN PATENT DOCUMENTS

| CN | 1088956 | 7/1994 |
| CN | 1719254 | 1/2006 |
| CN | 102311730 | 1/2012 |
| CN | 102329611 | 1/2012 |
| CN | 103288802 | 9/2013 |
| CN | 103575899 | 2/2014 |
| CN | 103772433 | 5/2014 |
| CN | 104597233 | 5/2015 |
| JP | 2002293775 | 10/2002 |

OTHER PUBLICATIONS

Huang et al. Antibacterial activity evaluation of quaternary chitin against *Escherichia coli* and *Staphylococcus aureus*. International Journal of Biological Macromolecules 2013, vol. 52, pp. 85-91. (Year: 2013).*
International Search Report, issued in the corresponding International PCT Application No. PCT/CN2015/096022, dated Feb. 26, 2016, 10 pages.
Fan et al., "Synthesis of a Cationic Glucosamine Surfactant and Study on its Performance", Chemistry and Bioengineering, vol. 27, No. 7, Jul. 25, 2010, 4 pages (cited in the International Search Report, English Title and Abstract provided in document).

* cited by examiner

*Primary Examiner* — Shafiqul Haq
(74) *Attorney, Agent, or Firm* — Hamre, Schumann, Mueller & Larson, P.C.

(57) ABSTRACT

Disclosed are an enhancement solution for enhancing chemiluminescence, and a method for preparing a chemiluminescent solution. The method comprises Step A: dissolving methylglucamine in water, adjusting the pH to 8-9, then adding an N-alkyldimethylmannosamine quaternary ammonium salt, acridine orange, BSA, glycine, $MgCl_2$, and $ZnCl_2$ respectively to a diethanolamine solution, stirring to dissolve them, and diluting to a constant volume, to obtain an enhancement solution; and Step B: diluting a chemiluminescent substrate with the enhancement solution, to obtain a chemiluminescent solution. When used in the field of immunoassays, the enhancement solution of the present invention increases the sensitivity and linear range of detection, reduces the cost, and is free of contamination.

6 Claims, 4 Drawing Sheets

ENHANCEMENT SOLUTION FOR ENHANCING CHEMILUMINESCENCE AND METHOD FOR PREPARING CHEMILUMINESCENT SOLUTION

This application is a continuation of PCT/CN2015/096022, filed on Nov. 30, 2015. The contents of PCT/CN2015/096022 are all hereby incorporated by reference.

BACKGROUND OF THE INVENTION

Field of the Invention

The present application relates to an enhancement solution for enhancing chemiluminescence and a method for preparing a chemiluminescent solution.

Related Arts

Chemiluminescence, as an immunoassay technology that is rapidly developed and widely used at abroad recently, has the characteristics of high sensitivity, wide linear range of detection, absence of contamination, and others. At present, the existing chemiluminescent immunoassays mainly include, for example, luminol, isoluminol, acridine, and dioxetane derivative (e.g. CSPD, CDP-SATR, and AMPPD) systems. The acridine and isoluminol are directly labeled for tracing, and thus are of direct chemiluminescence. The luminal and the dioxetane derivatives (e.g. CSPD, CDP-SATR, and AMPPD) are of enzymatic chemiluminescence. CSPD, CDP-SATR, AMPPD, and their enhancement solutions are mostly imported and highly expensive.

U.S. Pat. No. 5,145,772 discloses the luminescence enhancing effect of poly(vinylbenzyl(benzyldimethylammonium chloride)) micelles on dioxetane compounds. U.S. Pat. No. 5,547,836 discloses the luminescence enhancement of dioxetane compounds by poly(vinylbenzyltrimethylammonium chloride). Chinese Patent No. CN1719254A discloses a luminescent solution having CSPD as a substrate, and cetyltrimethylammonium chloride, BSA, octadecyl fluorescein, and 1,2-dimyristoyl-Sn-glycero-3-phosphate disodium salt (DGPD) as an enhancement solution. However, the cost is high, and the preparation is complex, which are not conducive to the wide use of the product.

SUMMARY

The present application provides an enhancement solution for enhancing chemiluminescence, comprising at least an N-alkyldimethylmannosamine quaternary ammonium salt having a structural formula below:

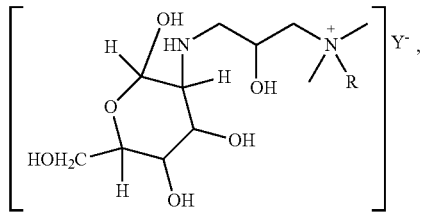

where R is a C8-40 alkyl or C8-40 alkenyl, Y is a negative ion; and
1-50 mg/L acridine orange, 1-100 g/L BSA, 1-10 g/L glycine, 0.1-0.5 mol/L methylglucamine, 0.1-10 mmol/L magnesium chloride or magnesium acetate, and 0.1-10 mmol/L zinc chloride.

The technical solution adopted in the present application has the advantages of increased sensitivity and linear range of detection, reduced cost, and absence of contamination, when the enhancement solution is used in the field of immunoassays, thereby solving the previous problems that the reagent is imported, expensive, and unable to achieve a desirable luminance performance, and others.

Preferably, the N-alkyldimethylmannosamine quaternary ammonium salt is at least one of N-dodecyldimethylmannosamine ammonium chloride, N-tetradecyldimethylmannosamine ammonium chloride, N-hexadecyldimethylmannosamine ammonium chloride, N-octadecyldimethylmannosamine ammonium chloride, N-dodecyldimethylmannosamine ammonium bromide, N-tetradecyldimethylmannosamine ammonium bromide, N-hexadecyldimethylmannosamine ammonium bromide, and N-octadecyldimethylmannosamine ammonium bromide.

Preferably, the methylglucamine has a pH of 8.5.

The present application further provides a method for preparing a chemiluminescent solution with the enhancement solution, comprising:

Step A: dissolving methylglucamine in water, adjusting the pH to 8-9, then adding an N-alkyldimethylmannosamine quaternary ammonium salt, acridine orange, BSA, glycine, $MgCl_2$, and $ZnCl_2$ respectively to a diethanolamine solution, stirring to dissolve them, and diluting to a constant volume, to obtain an enhancement solution; and Step B: diluting a chemiluminescent substrate with the enhancement solution, to obtain a chemiluminescent solution.

Preferably, the chemiluminescent substrate is a dioxetane compound.

Preferably, the chemiluminescent substrate is 9-[3-(5-chloro-2-spiroadamantane)-1,2-dioxetane]-3-chloro-7-phosphoryloxy-10-propionyloxy-9,10-dihydroacridine disodium salt,
having a structural formula of

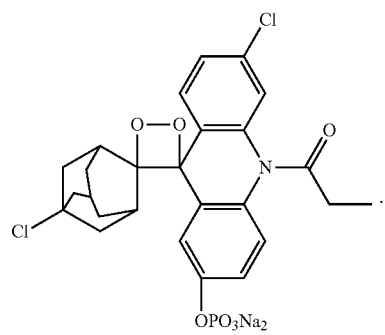

The present application has the following beneficial effects.

1: Compared with a commercially available enhancement solution, the stability of a chemiluminescent solution containing a dioxetane compound as a chemiluminescent substrate is increased.

2: Compared with a commercially available enhancement solution, the performance of a chemiluminescent solution containing a dioxetane compound as a chemiluminescent substrate is increased is enhanced.

3: Compared with the commercially available CDP-STAR+ Emerald-II™, the luminescent signal of a chemiluminescent solution is considerably increased.

4: Compared with the commercially available CDP-STAR+ Emerald-II™, the detection time of a chemiluminescent solution is obviously shortened.

5: Compared with an imported chemiluminescent solution and enhancer, the product of the present application is much economical, and has a high sensitivity, a high stability and a low price.

BRIEF DESCRIPTION OF THE DRAWINGS

The present application will become more fully understood from the detailed description given herein below for illustration only, and thus are not limitative of the present application, and wherein:

FIG. 5b is a partially enlarged schematic view of FIG. 5a.

DETAILED DESCRIPTION OF THE INVENTION

Figure 1:
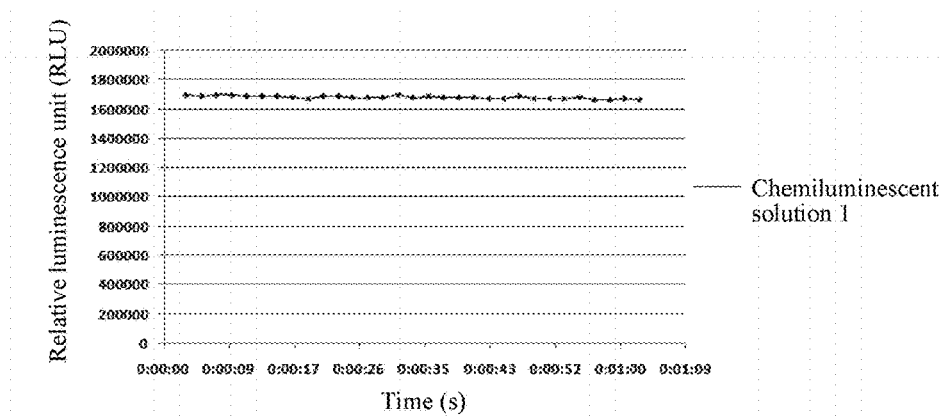
FIG. 1 is a luminescence kinetic graph detected in Example 1 where 10 µl of $2*10^{-16}$ mol alkaline phosphatase is added as a sample to a microplate, then 100 µl of a chemiluminescent solution 1 is added, and the luminescent signal is recorded on a chemiluminescence analyzer (BIOTEK-Synergy2).

The present application is described in further detail below with reference to embodiments and the accompanying drawings.

EXAMPLE 1

Step 1: 19.5 g of methylglucamine was dissolved in 900 mL of water, and the pH was adjusted to 8.5. 1 g of N-dodecyldimethylmannosamine ammonium chloride, 6 mg of acridine orange, 10 g of BSA, 30 mg of glycine, 1 mmol of $MgCl_2$, and 0.2 mmol of $ZnCl_2$ were added respectively to a diethanolamine solution, stirred to dissolve them, and diluted to a constant volume of 1 L, to obtain an enhancement solution (1).

Step 2:
9-[3-(5-chloro-2-spiroadamantane)-1,2-dioxetane]-3-chloro-7-phosphoryloxy-10-propi onyloxy-9,10-dihydroacridine disodium salt was diluted to 450 mg/L with the enhancement solution (1), to obtain a chemiluminescent solution 1.

Step 3:
9-[3-(5-chloro-2-spiroadamantane)-1,2-dioxetane]-3-chloro-7-phosphoryloxy-10-propi onyloxy-9, 10-dihydroacridine disodium salt was diluted to 450 mg/L with the enhancement solution Emerald-II™ (Tropix), to obtain a chemiluminescent solution 2.

Step 4: CDP-STAR was diluted to 400 mg/L with the enhancement solution (1), to obtain a chemiluminescent solution 3.

Step 5: CDP-STAR was diluted to 400 mg/L with the enhancement solution Emerald-II™ (Tropix), to obtain a chemiluminescent solution 4.

Test Steps:
1. 10 µl of $2*10^{-16}$ mol alkaline phosphatase was added as a sample to a microplate, then 100 µl of the chemiluminescent solution 1 was added, and the luminescent signal was recorded on a chemiluminescence analyzer (BIOTEK-Synergy2), to detect the luminescence kinetic graph, as shown in FIG. 1.

Figure 2:
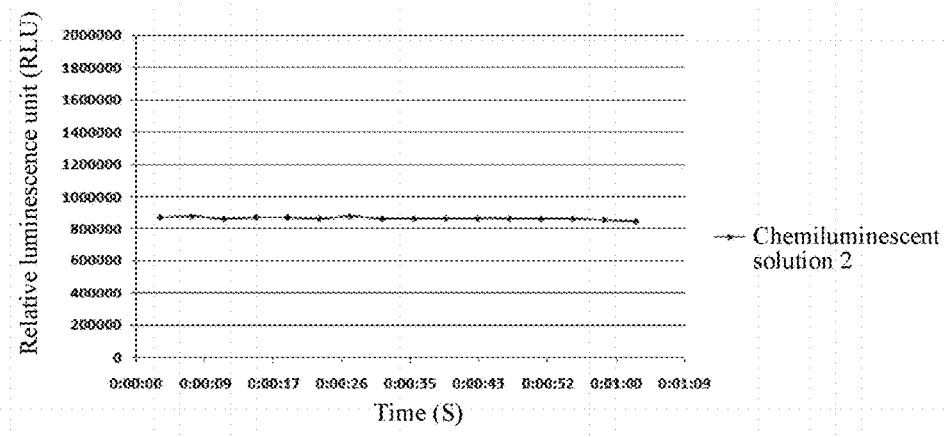
FIG. 2 is a luminescence kinetic graph detected in Example 1 where 10 µl of $2*10^{-16}$ mol alkaline phosphatase is added as a sample to a microplate, then 100 µl of a chemiluminescent solution 2 is added, and the luminescent signal is recorded on a chemiluminescence analyzer (BIOTEK-Synergy2).

2. 10 µl of $2*10^{-16}$ mol alkaline phosphatase was added as a sample to a microplate, then 100 µl of the chemiluminescent solution 2 was added, and the luminescent signal was recorded on a chemiluminescence analyzer (BIOTEK-Synergy2), to detect the luminescence kinetic graph, as shown in FIG. 2.

Figure 3:
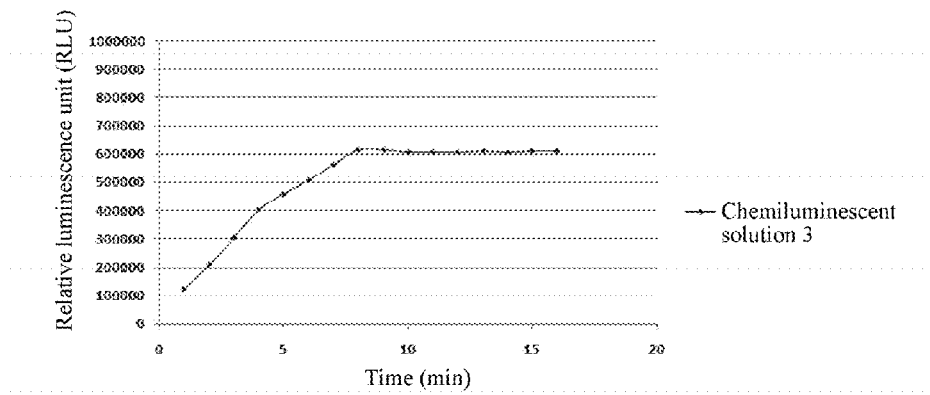
FIG. 3 is a luminescence kinetic graph detected in Example 1 where 10 µl of $2*10^{-16}$ mol alkaline phosphatase is added as a sample to a microplate, then 100 µl of a chemiluminescent solution 3 is added, and the luminescent signal is recorded on a chemiluminescence analyzer (BIOTEK-Synergy2).

3. 10 µl of $2*10^{-16}$ mol alkaline phosphatase was added as a sample to a microplate, then 100 µl of the chemiluminescent solution 3 was added, and the luminescent signal was recorded on a chemiluminescence analyzer (BIOTEK-Synergy2), to detect the luminescence kinetic graph, as shown in FIG. 3.

Figure 4:
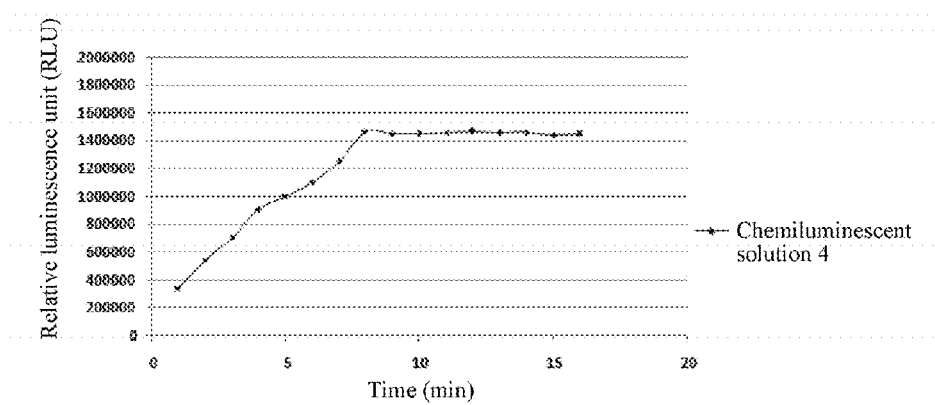
FIG. 4 is a luminescence kinetic graph detected in Example 1 where 10 µl of $2*10^{-16}$ mol alkaline phosphatase is added as a sample to a microplate, then 100 µl of a chemiluminescent solution 4 is added, and the luminescent signal is recorded on a chemiluminescence analyzer (BIOTEK-Synergy2).

4. 10 µl of $2*10^{-16}$ mol alkaline phosphatase was added as a sample to a microplate, then 100 µl of the chemiluminescent solution 4 was added, and the luminescent signal was recorded on a chemiluminescence analyzer (BIOTEK-Synergy2), to detect the luminescence kinetic graph, as shown in FIG. 4.

It can be known from FIGS. 1 and 2 that when the enhancement solution (1) and Emerald-II™ (Tropix) are used in a chemiluminescent substrate A containing a dioxetane compound, the chemiluminescent solution 2 formulated with Emerald-II™ has a luminescence efficiency that is obviously lower than that of the chemiluminescent solution 1 formulated with the enhancement solution (1).

It can be known from FIGS. 3 and 4 that when the enhancement solution (1) and Emerald-II™ (Tropix) are used in the dioxetane compound CDP-STAR, the chemiluminescent solution 4 formulated with Emerald-II™ has a luminescence efficiency that is obviously higher than that of the chemiluminescent solution 3 formulated with the enhancement solution (1).

EXAMPLE 2

Step 1: 19.5 g of methylglucamine was dissolved in 900 mL of water, and the pH was adjusted to 8.5. 1 g of N-dodecyldimethylmannosamine ammonium chloride, 6 mg of acridine orange, 10 g of BSA, 1 mmol of $MgCl_2$, and 0.2 mmol of $ZnCl_2$ were added respectively to a diethanolamine solution, stirred to dissolve them, and diluted to a constant volume of 1 L, to obtain an enhancement solution (2).

Step 2:
9-[3-(5-chloro-2-spiroadamantane)-1,2-dioxetane]-3-chloro-7-phosphoryloxy-10-propi onyloxy-9, 10-dihydroacridine disodium salt(A) was diluted to 450 mg/L with the enhancement solution (2), to obtain a chemiluminescent solution 5.

Step 3: The chemiluminescent solution 1 obtained in Example 1 was divided into two portions: a chemiluminescent solution 1-A and a chemiluminescent solution 1-B. The chemiluminescent solution 1-B was stored at 37° C. for 6 days, and the chemiluminescent solution 1-A was stored at room temperature for 6 days.

Step 4: The chemiluminescent solution 2 obtained in Example 1 was divided into two portions: a chemiluminescent solution 2-A and a chemiluminescent solution 2-B. The chemiluminescent solution 2-B was stored at 37° C. for 6 days, and the chemiluminescent solution 2-A was stored at room temperature for 6 days.

Step 5: The chemiluminescent solution 5 was divided into two portions: a chemiluminescent solution 5-A and a chemiluminescent solution 5-B. The chemiluminescent solution 5-B was stored at 37° C. for 6 days, and the chemiluminescent solution 5-A was stored at room temperature for 6 days.

Test Method:
Step A: 10 μl of $2*10^{-16}$ 1 mol alkaline phosphatase was added as a sample to a microplate, then 100 μl of the chemiluminescent solution 1-A, the chemiluminescent solution 1-B, the chemiluminescent solution 5-A, and the chemiluminescent solution 5-B were added respectively, and the luminescent signal was recorded on a chemiluminescence analyzer (BIOTEK-Synergy2), to detect the luminescence kinetic graphs, as shown in FIGS. 5a and 5b.

Figure 6:
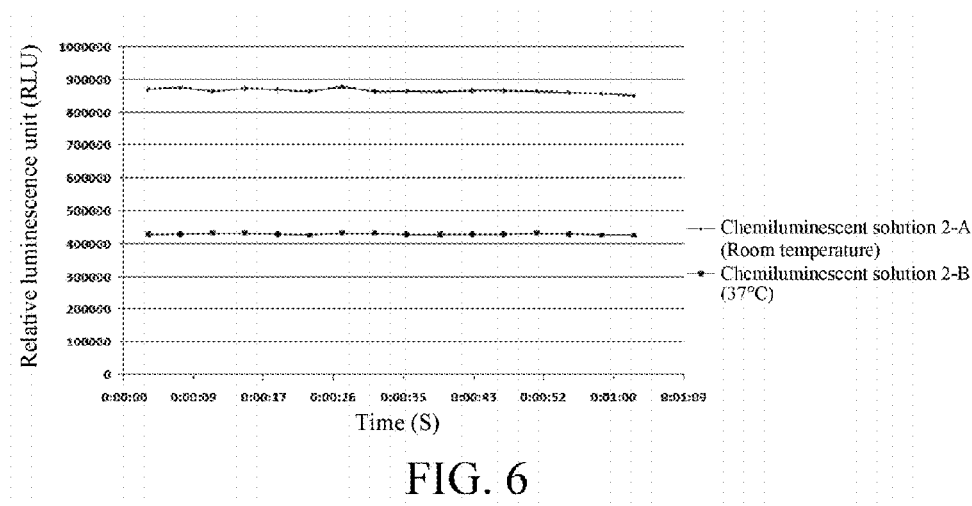
FIG. 6 is a luminescence kinetic graph detected in Example 2 where 10 µl of $2*10^{-16}$ mol alkaline phosphatase is added as a sample to a microplate, then 100 µl of a chemiluminescent solution 2-A, and a chemiluminescent solution 2-B are added respectively, and the luminescent signal is recorded on a chemiluminescence analyzer (BIOTEK-Synergy2).

10 μl of $2*10^{-16}$ mol alkaline phosphatase was added as a sample to a microplate, then 100 μl of the chemiluminescent solution 2-A, the chemiluminescent solution 2-B were added respectively, and the luminescent signal was recorded on a chemiluminescence analyzer (BIOTEK-Synergy2), to detect the luminescence kinetic graphs, as shown in FIG. 6.

Figure 5A:
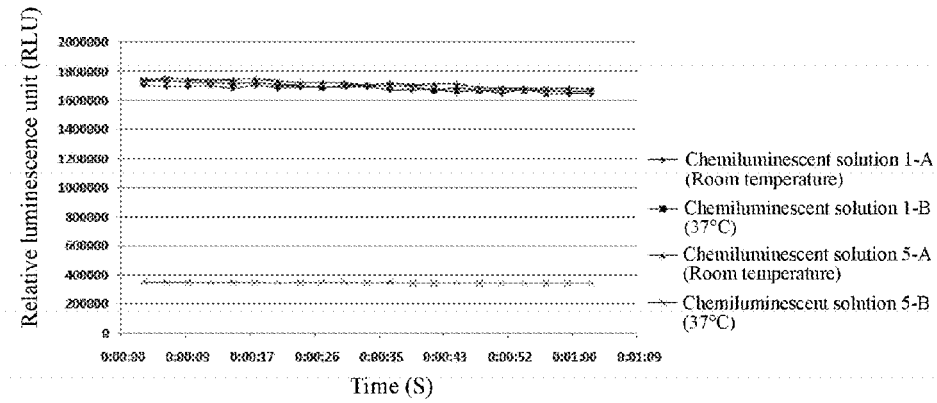
FIG. 5a is a luminescence kinetic graph detected in Example 2 where 10 µl of $2*10^{-16}$ mol alkaline phosphatase is added as a sample to a microplate, then 100 µl of a chemiluminescent solution 1-A, a chemiluminescent solution 1-B, a chemiluminescent solution 5-A, and a chemiluminescent solution 5-B are added respectively, and the luminescent signal is recorded on a chemiluminescence analyzer (BIOTEK-Synergy2).
Figure 5B:
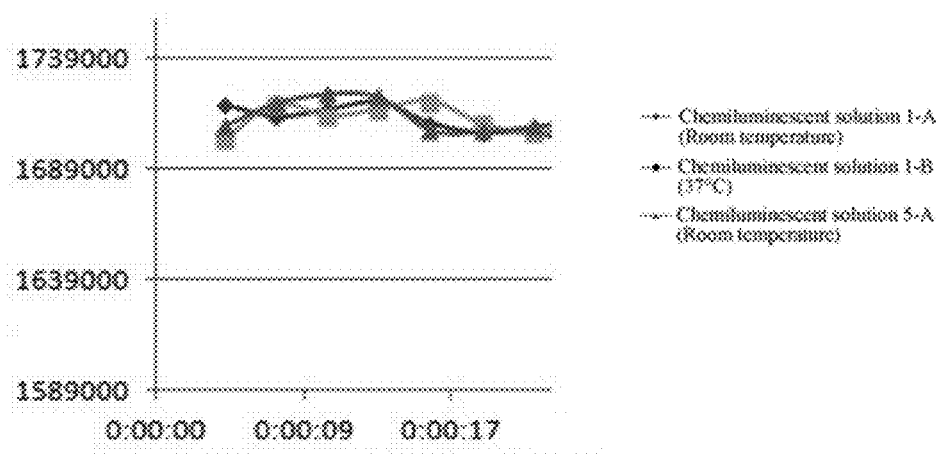

It can be known from FIGS. 5a and 5b that after the chemiluminescent solution 1 is stored respectively at room temperature and 37° C. for 6 days, the luminescent signal is substantially unchanged; in contrast, after the chemiluminescent solution 5 is stored respectively at room temperature and 37° C. for 6 days, the luminescent signal from the chemiluminescent solution 5-B stored at 37° C. declines obviously. Therefore, glycine is found to synergistically increase the stability of the chemiluminescent solution.

It can be known from FIG. 6 that after storage at 37° C. for 6 days, the luminescent signal from the chemiluminescent solution 2 formulated with the luminescence enhancement solution Emerald-II™ (Tropix) declines obviously, compared with that stored at room temperature.

EXAMPLE 3

19.5 g of methylglucamine was dissolved in 900 mL of water, and the pH was adjusted to 8.5. 1 g of N-dodecyldimethylmannosamine ammonium chloride, 6 mg of acridine orange, 10 g of BSA, 30 mg of glycine, and 1 mmol of $MgCl_2$ were added respectively to a diethanolamine solution, stirred to dissolve them, and diluted to a constant volume of 1 L, to obtain an enhancement solution (3).

9-[3-(5-chloro-2-spiroadamantane)-1,2-dioxetane]-3-chloro-7-phosphoryloxy-10-propi onyloxy-9, 10-dihydroacridine disodium salt (A) was diluted to 450 mg/L with the enhancement solution (3), to obtain a chemiluminescent solution 6.

10 μl of $2*10^{-16}$ mol alkaline phosphatase was added as a sample to a microplate, then 100 μl of the chemiluminescent solution 1 and the chemiluminescent solution 6 were added respectively, and the luminescent signal was recorded on a chemiluminescence analyzer (BIOTEK-Synergy2), to detect the luminescence kinetic graph.

Figure 7:
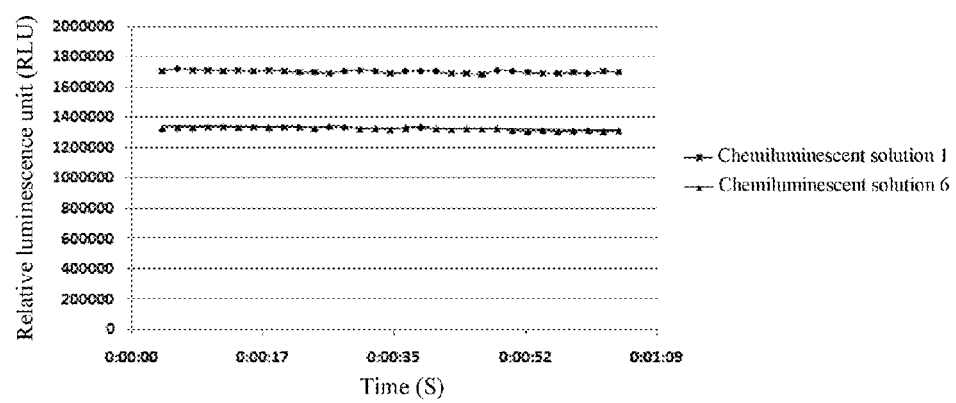
FIG. 7 is a luminescence kinetic graph detected in Example 3 where 10 µl of $2*10^{-16}$ mol alkaline phosphatase is added as a sample to a microplate, then 100 µl of a chemiluminescent solution 1, and a chemiluminescent solution 6 are added respectively, and the luminescent signal is recorded on a chemiluminescence analyzer (BIOTEK-Synergy2).

As shown in FIG. 7, the luminescent signal from the chemiluminescent solution 1 is obviously higher than that from the chemiluminescent solution 6. Therefore, it is found in the present application that $ZnCl_2$ can enhance the luminescent signal.

Although the present application is described above in further detail through specific embodiments, the present application is not limited to the specific embodiments. It should be understood by persons of ordinary skill in the art that any simple deduction or replacement made without departing from the spirit of the present application shall fall within the protection scope of the present application.

What is claimed is:
1. An enhancement solution for enhancing chemiluminescence, comprising at least an N-alkyldimethylmannosamine quaternary ammonium salt having a structural formula below:

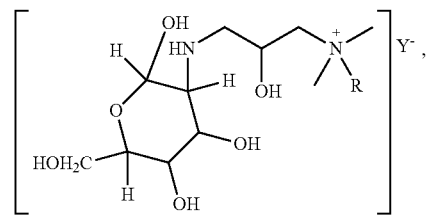

wherein R is a C8-40 alkyl or a C8-40 alkenyl, Y is a negative ion; and
1-50 mg/L acridine orange, 1-100 g/L BSA, 1-10 g/L glycine, 0.1-0.5 mol/L methylglucamine, 0.1-10 mmol/L magnesium chloride or magnesium acetate, and 0.1-10mmol/L zinc chloride.

2. The enhancement solution according to claim 1, wherein the N-alkyldimethylmannosamine quaternary ammonium salt is at least one of N-dodecyldimethylmannosamine ammonium chloride, N-tetradecyldimethylmannosamine ammonium chloride, N-hexadecyldimethylmannosamine ammonium chloride, N-octadecyldimethylmannosamine ammonium chloride, N-dodecyldimethylmannosamine ammonium bromide, N-tetradecyldimethylmannosamine ammonium bromide, N-hexadecyldimethylmannosamine ammonium bromide, and N-octadecyldimethylmannosamine ammonium bromide.

3. The enhancement solution according to claim 1, wherein the methylglucamine has a pH of 8.5.

4. A method for preparing a chemiluminescent solution with the enhancement solution according to claim 1, comprising:

Step A: dissolving methylglucamine in water, adjusting the pH to 8-9, then adding an N-alkyldimethylmannosamine quaternary ammonium salt of the structural formula of claim 1, acridine orange, BSA, glycine, $MgCl_2$, and $ZnCl_2$ respectively to a diethanolamine solution, stirring to dissolve them, and diluting to a constant volume, to obtain an enhancement solution; and Step B: diluting a chemiluminescent substrate with the enhancement solution, to obtain a chemiluminescent solution.

5. The method according to claim 4, wherein in Step B, the chemiluminescent substrate is a dioxetane compound.

6. The method according to claim 4, wherein in Step B, the chemiluminescent substrate is 9-[3-(5-chloro-2-spiro-adamantane)-1,2-dioxetane]-3-chloro-7-phosphoryloxy-10-propionyloxy-9,10-dihydroacridine disodium salt, having a structural formula below:

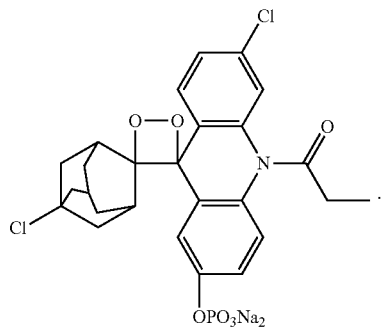

* * * * *